United States Patent [19]

Gehring et al.

[11] Patent Number: 4,863,937
[45] Date of Patent: Sep. 5, 1989

[54] 1-ARYLPYRAZOLES, PESTICIDAL COMPOSITIONS AND USE

[75] Inventors: Reinhold Gehring, Wuppertal; Uta Korte-Jensen, Duesseldorf; Otto Schallner, Monheim; Jörg Stetter, Wuppertal; Benedikt Becker, Mettmann; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 223,188

[22] Filed: Jul. 22, 1988

[30] Foreign Application Priority Data

Jul. 28, 1987 [DE] Fed. Rep. of Germany ....... 3724919

[51] Int. Cl.$^4$ .................. A01N 43/56; C07D 231/44; C07D 401/04; C07D 401/12
[52] U.S. Cl. .................... 514/333; 514/341; 514/407; 546/256; 546/279; 548/374; 548/376
[58] Field of Search ............... 546/256, 279; 548/374, 548/376; 514/333, 341, 407

[56] References Cited

U.S. PATENT DOCUMENTS 4,771,066  9/1988  Gehring et al. ..................... 514/407

Primary Examiner—Robert W. Ramsuer
Attorney, Agent, or Firm—Sprung, Horn, Kramer & Woods

[57] ABSTRACT

Pest-combating agents, especially as insecticides, which are 1-arylpyrazoles of the formula in which
$R^1$ represents hydrogen, alkyl or halogenoalkyl,
$R^2$ represents alkyl, halogenoalkyl, optionally substituted aralkyl or optionally substituted aryl,
$R^3$ represents hydrogen, alkyl or halogenoalkyl,
$R^4$ represents alkyl, alkenyl, alkinyl, halogenoalkyl, halogenoalkenyl, halogenoalkinyl or in each case optionally substituted aryl or heteroaryl,
X represents oxygen, sulphur or an N-alkyl radical,
Ar represents in each case optionally substituted phenyl or pyridyl,
m represents a number 0 or 1 and
n represents a number 0, 1 or 2,
have been found.

7 Claims, No Drawings

1-ARYLPYRAZOLES, PESTICIDAL COMPOSITIONS AND USE

The invention relates to new 1-arylpyrazoles, several processes for their preparation and their use as pest-combating agents.

It has already been disclosed that certain 1-arylpyrazoles such as, for example, 5-(N-methylamino)-4-trifluoromethylthio-1-(2,6-dichloro-4-trifluoromethylphenyl)-pyrazole or 5-(N-methylamino)-4-dichlorofluoromethylthio-1-(2,6-dichloro-4-trifluoromethylphenyl)pyrazole possess good insecticidal properties (compare EP No. 201,852).

However, the activity of these previously known compounds is not completely satisfactory against all harmful insects nor in all areas of use, in particular at low application rates and concentrations.

New 1-arylpyrazoles of the general formula (I)

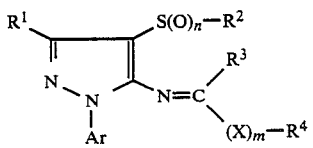

in which
$R^1$ represents hydrogen, alkyl or halogenoalkyl,
$R^2$ represents alkyl, halogenoalkyl, optionally substituted aralkyl or optionally substituted aryl,
$R^3$ represents hydrogen, alkyl or halogenoalkyl,
$R^4$ represents alkyl, alkenyl, alkinyl, halogenoalkyl, halogenoalkenyl, halogenoalkinyl or in each case optionally substituted aryl or heteroaryl,
X represents oxygen, sulphur or an N-alkyl radical,
Ar represents in each case optionally substituted phenyl or pyridyl,
m represents a number 0 or 1 and
n represents a number 0, 1 or 2,
have been found.

Furthermore, it has been found that the new 1-arylpyrazoles of the general formula (I)

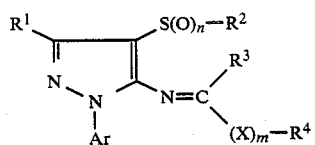

in which
$R^1$ represents hydrogen, alkyl or halogenoalkyl,
$R^2$ represents alkyl, halogenoalkyl, optionally substituted aralkyl or optionally substituted aryl,
$R^3$ represents hydrogen, alkyl or halogenoalkyl,
$R^4$ represents alkyl, alkenyl, alkinyl, halogenoalkyl, halogenoalkenyl, halogenoalkinyl or in each case optionally substituted aryl or heteroaryl,
X represents oxygen, sulphur or an N-alkyl radical,
Ar represents in each case optionally substituted phenyl or pyridyl,
m represents a number 0 or 1 and
n represents a number 0, 1 or 2,
are obtained by one of the processes described below:
(a) 1-arylpyrazoles of the formula (Ia)

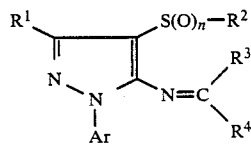

in which $R^1$, $R^2$, $R^3$, $R^4$, Ar and n have the abovementioned meaning, are obtained when 5-amino-1-arylpyrazoles of the formula (II)

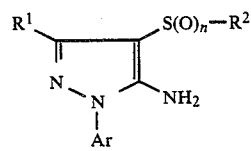

in which $R^1$, $R^2$, Ar and n have the abovementioned meaning, are reacted with aldehydes or ketones of the formula (III)

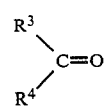

in which $R^3$ and $R^4$ have the abovementioned meaning, if appropriate in the presence of a diluent and if appropriate in the presence of a reaction auxiliary;

(b) 1-arylpyrazoles of the formula (Ib)

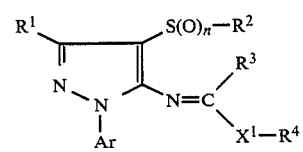

in which
$X^1$ represents oxygen or an N-alkyl radical and
$R^1$, $R^2$, $R^3$, $R^4$, Ar and n have the abovementioned meaning,
are obtained when 5-amino-1-arylpyrazoles of the formula (II)

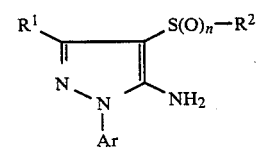

in which $R^1$, $R^2$, Ar and n have the abovementioned meaning, are reacted with orthoesters or orthoamides of the formula (IV)

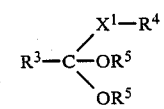

in which
$R^5$ represents alkyl and
$R^3$, $R^4$ and $X^1$ have the abovementioned meaning, if appropriate in the presence of a diluent and if appropriate in the presence of a reaction auxiliary;

(c) 1-arylpyrazoles of the formula (Ic)

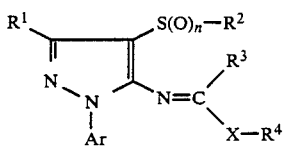

in which
R$^1$, R$^2$, R$^3$, R$^4$, X, Ar and n have the abovementioned meaning,
are obtained when 5-halogenoalkylideneimino-1-arylpyrazoles of the formula (V)

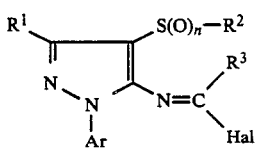

in which
R$^1$, R$^2$, R$^3$, Ar and n have the abovementioned meaning and
Hal represents halogen,
are reacted with alcohols, amines or thiols of the formula (VI)

$$R^4—XH \qquad (VI)$$

in which R$^4$ and X have the abovementioned meaning,
if appropriate in the presence of a diluent and if appropriate in the presence of a reaction auxiliary;

(d) 1-arylpyrazoles of the formula (Id)

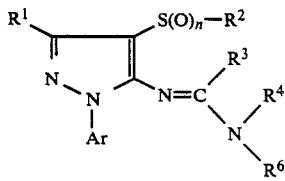

in which
R$^6$ represents alkyl and
R$^1$, R$^2$, R$^3$, R$^4$, Ar and n have the abovementioned meaning,
are obtained when 1-arylpyrazoles of the formula (Ie)

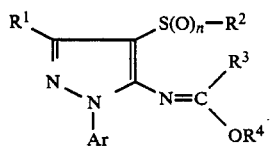

in which R$^1$, R$^2$, R$^3$, R$^4$, Ar and n have the abovementioned meaning, are reacted with amines of the formula (VII)

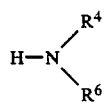

in which R$^4$ and R$^6$ have the abovementioned meaning, if appropriate in the presence of a diluent.

Finally, it has been found that the new 1-arylpyrazoles of the general formula (I) possess a good action against pests.

Surprisingly, the 1-arylpyrazoles of the general formula (I), according to the invention, show a considerably better insecticidal activity than the 1-arylpyrazoles known from the prior art, such as, for example, 5-(N-methylamino)-4-trifluoromethylthio-1-(2,6-dichloro-4-trifluoromethylphenyl)pyrazole or 5-(N-methylamino)-4-dichlorofluoromethylthio-1-(2,6-dichloro-4-trifluoromethylphenyl)-pyrazole, which are similar compounds chemically and in terms of their action.

Formula (I) provides a general definition of the 1-arylpyrazoles according to the invention. Preferred are compounds of the formula (I) in which R$^1$ represents hydrogen or in each case straight-chain or branched alkyl or halogenoalkyl having in each case 1 to 4 carbon atoms and where appropriate 1 to 9 identical or different halogen atoms, R$^2$ represents straight-chain or branched alkyl having 1 to 8 carbon atoms, straight-chain or branched halogenoalkyl having 1 to 8 carbon atoms and 1 to 17 identical or different halogen atoms, or phenylalkyl or phenyl where appropriate having 1 to 4 carbon atoms in the straight-chain or branched alkyl part and in each case being optionally monosubstituted or polysubstituted in the phenyl part by identical or different substituents, suitable substituents in the phenyl part in each case being: halogen, cyano, nitro, in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl having in each case 1 to 4 carbon atoms in the individual alkyl parts and where appropriate 1 to 9 identical or different halogen atoms, R$^3$ represents hydrogen or in each case straight-chain or branched alkyl or halogenoalkyl having in each case 1 to 8 carbon atoms and where appropriate 1 to 17 identical or different halogen atoms, R$^4$ represents in each case straight-chain or branched alkyl, alkenyl or alkinyl having in each case up to 8 carbon atoms, in each case straight-chain or branched halogenoalkyl, halogenoalkenyl or halogenoalkinyl having in each case up to 8 carbon atoms and 1 to 17 identical or different halogen atoms, or phenyl or heteroaryl having 1 to 9 carbon atoms and 1 to 3 hetero atoms, in particular nitrogen, oxygen and/or sulphur and in each case being optionally monosubstituted or polysubstituted by identical or different substituents, suitable substituents in each case being the substituents mentioned as phenyl substituents for R$^2$, X represents oxygen, sulphur or an N-alkyl radical having 1 to 6 carbon atoms in the straight-chain or branched alkyl part, Ar represents phenyl, 2-pyridyl, 3-pyridyl or 4-pyridyl which is in each case optionally monosubstituted or polysubstituted by identical or different substituents, suitable substituents in each case being: cyano, nitro, halogen, in each case straight-chain or branched alkyl, alkoxy or alkoxycarbonyl having in each case 1 to 4 carbon atoms, in each case straight-chain or branched halogenoalkyl or halogenoalkoxy having in each case 1 to 4 carbon atoms and 1 to 9 identical or different halogen atoms or a radical —S(O)$_p$—R$^7$, in which R⁷ represents amino, and also in each case straight-chain or branched alkyl, alkylamino, dialkylamino or halogenoalkyl having in each case 1 to 4 carbon atoms in the individual alkyl parts and in the case of halogenoalkyl having 1 to 9 identical or different halogen atoms, m represents a number 0 or 1, n represents a number 0, 1 or 2 and p represents a number 0, 1 or 2.

Particularly preferred compounds of the formula (I) are those in which

R¹ represents hydrogen, methyl, ethyl, n- or i-propyl and trifluoromethyl,

R² represents methyl, ethyl, n- or i-propyl, n-, i-, s- or t-butyl, n- or i-pentyl, n- or i-hexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, or phenyl, benzyl or phenylethyl which is in each case optionally monosubstituted, disubstituted or trisubstituted by identical or different substituents, suitable phenyl substituents in each case being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, R³ represents hydrogen, methyl, ethyl, n- or i-propyl, n-, i-, s- or t-butyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, dichloromethyl, chloropropyl, bromopropyl, chlorofluoromethyl, trichloromethyl, trifluoroethyl, trifluorochloroethyl, tetrafluoroethyl, difluorochloroethyl, fluorodibromomethyl, difluorobromomethyl or fluorochlorobromomethyl, R⁴ represents methyl, ethyl, n- or i-propyl, n-, i-, s- or t-butyl, n- or i-pentyl, n- or i-hexyl, vinyl, propenyl, allyl, n- or i-butenyl, n- or i-pentenyl, propargyl, n- or i-butinyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl, fluoroallyl, chlorobutenyl, fluorobutenyl, dichloroallyl, fluorochloroallyl, dichlorobutenyl, difluoroallyl, bromoallyl, or phenyl, pyridyl, furyl or thienyl which is in each case optionally monosubstituted, disubstituted or trisubstituted by identical or different substituents, suitable substituents in each case being the substituents mentioned as phenyl substituents for R², X represents oxygen, sulphur or an N-alkyl radical having 1 to 4 carbon atoms in the straight-chain or branched alkyl part, Ar represents phenyl which is optionally monosubstituted to pentasubstituted by identical or different substituents or 2-pyridyl which is optionally monosubstituted to tetrasubstituted by identical or different substituents, suitable substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —S(O)ₚ—R⁷ in which R⁷ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, m represents a number 0 or 1, n represents a number 0, 1 or 2 and p represents a number 0, 1 or 2.

Very particularly preferred compounds of the formula (I) are those in which

R¹ represents hydrogen or methyl,

R² represents methyl, ethyl, trifluoromethyl, dichlorofluoromethyl or chlorodifluoromethyl, R³ represents hydrogen, methyl, ethyl, n- or i-propyl or trifluoromethyl, R⁴ represents methyl, ethyl, n- or i-propyl, n-, i-, s- or t-butyl, vinyl, propenyl, allyl, n- or i-butenyl, or phenyl which is optionally monosubstituted, disubstituted or trisubstituted identically or differently by fluorine, chlorine, bromine, methyl or trifluoromethyl substituents, X represents oxygen, sulphur, an N-methyl radical or an N-ethyl radical, Ar represents phenyl which is optionally monosubstituted to pentasubstituted by identical or different substituents, suitable substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl, m represents a number 0 or 1 and n represents a number 0, 1 or 2.

The following 1-arylpyrazoles of the general formula (I)

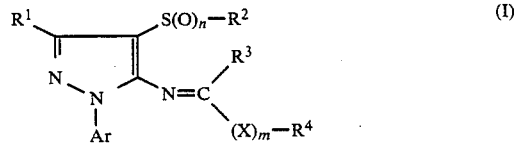

may be mentioned individually in addition to the compounds mentioned in the preparation examples:

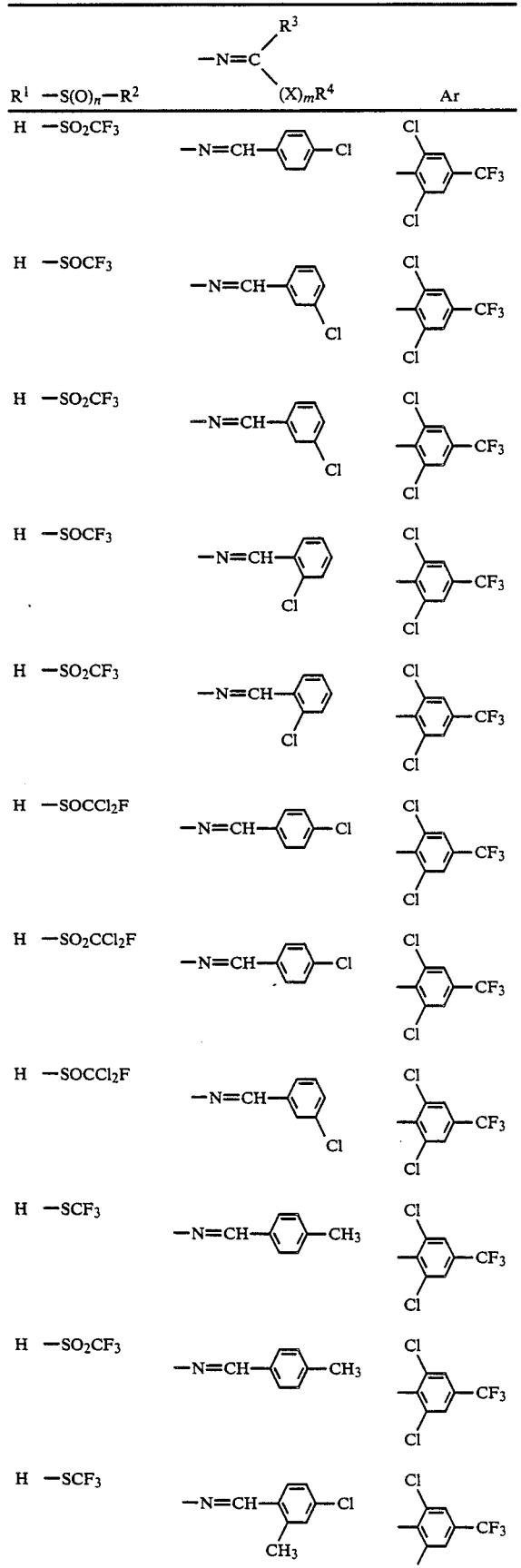

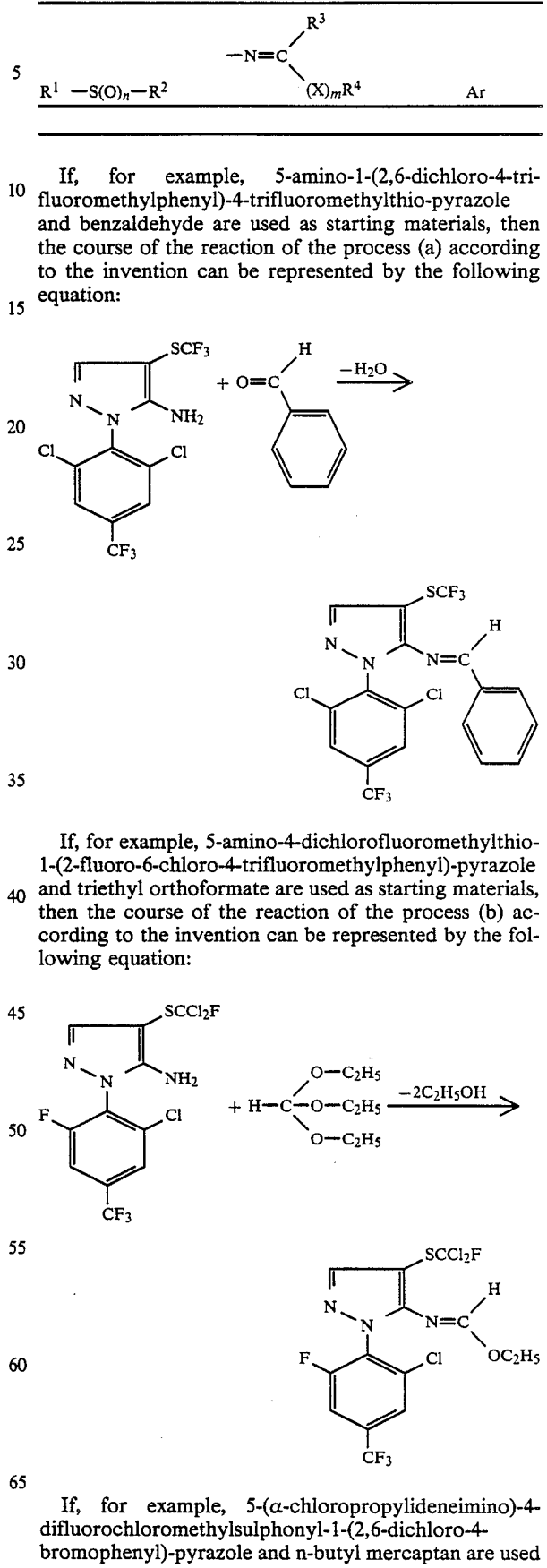

If, for example, 5-amino-1-(2,6-dichloro-4-tri-fluoromethylphenyl)-4-trifluoromethylthio-pyrazole and benzaldehyde are used as starting materials, then the course of the reaction of the process (a) according to the invention can be represented by the following equation:

If, for example, 5-amino-4-dichlorofluoromethylthio-1-(2-fluoro-6-chloro-4-trifluoromethylphenyl)-pyrazole and triethyl orthoformate are used as starting materials, then the course of the reaction of the process (b) according to the invention can be represented by the following equation:

If, for example, 5-(α-chloropropylideneimino)-4-difluorochloromethylsulphonyl-1-(2,6-dichloro-4-bromophenyl)-pyrazole and n-butyl mercaptan are used as starting materials, then the course of the reaction of the process (c) according to the invention can be represented by the following equation:

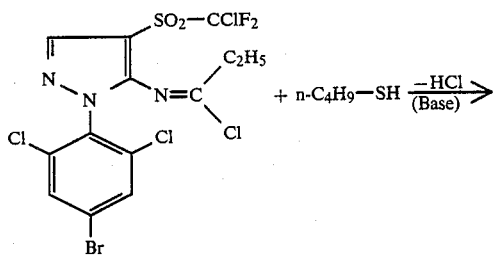

If, for example, 5-methoxymethylidene-imino-3-methyl-4-trifluoromethylsulphinyl-1-(4-trifluoromethylphenyl)-pyrazole and diethylamine are used as starting materials, then the course of the reaction of the process (d) according to the invention can be represented by the following equation:

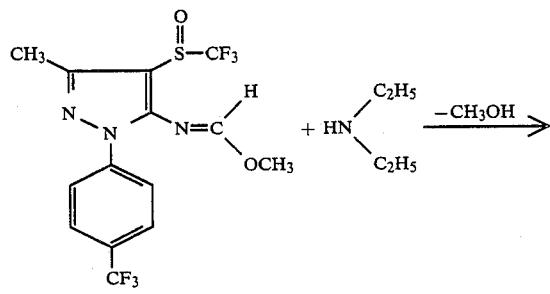

Formula (II) provides a general definition of the 5-amino-1-aryl-pyrazoles requires as starting materials for carrying out the processes (a) and (b) according to the invention. In this formula (II), $R^1$, $R^2$, Ar and n preferably represent those radicals which have already been mentioned as preferred for these substituents in connection with the description of the substances of the formula (I) according to the invention.

The 5-amino-1-aryl-pyrazoles of the formula (II) are known or can be prepared analogously to known processes (compare EP No. 201,852).

Formula (III) provides a general definition of the aldehydes or ketones furthermore required as starting materials for carrying out the process (a) according to the invention. In this formula (III), $R^3$ and $R^4$ preferably represent those radicals which have already been mentioned as preferred for these substituents in connection with the description of the substances of the formula (I) according to the invention.

The aldehydes or ketones of the formula (III) are generally known compounds of organic chemistry.

Formula (IV) provides a general definition of the orthoesters and orthoamides furthermore required as starting materials for carrying out the process (b) according to the invention. In this formula (IV), $R^3$ and $R^4$ preferably represent those radicals which have already been mentioned as preferred for these substituents in connection with the description of the substances of the formula (I) according to the invention.

$X^1$ preferably represents oxygen or a straight-chain or branched N-alkyl radical having 1 to 6, in particular having 1 to 4 carbon atoms.

$R^5$ preferably represents straight-chain or branched alkyl having 1 to 4 carbon atoms, in particular methyl or ethyl.

The orthoesters and orthoamides of the formula (IV) are generally known compounds of organic chemistry.

Formula (V) provides a general definition of the 5-halogenoalkylideneimino-1-arylpyrazoles required as starting materials for carrying out the process (c) according to the invention. In this formula (V), $R^1$, $R^2$, $R^3$, Ar and n preferably represent those radicals which have already been mentioned as preferred for these substituents in connection with the description of the substances of the formula (I) according to the invention.

Hal preferably represents chlorine or bromine.

The 5-halogenoalkylideneimino-1-aryl-pyrazoles of the formula (V) were hitherto unknown. They are obtained when 5-acylamino-1-aryl-pyrazoles of the formula (VIII)

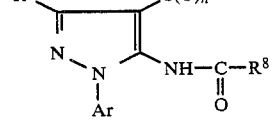

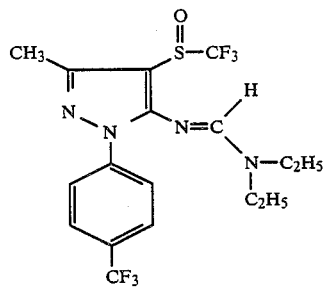

(VIII)

in which
$R^1$, $R^2$, Ar and n have the abovementioned meaning and $R^8$ represents alkyl, in particular methyl or ethyl, are reacted with customary halogenating agents, such as for example, phosphorus pentachloride or phosphorus tribromide, if appropriate in the presence of a diluent such as, for example, dichloromethane, at temperatures between 20° C. and 120°.

The 5-acylamino-1-arylpyrazoles of the formula (VIII) are known or can be prepared analogously to known processes (compare EP No. 201,852).

Formula (VI) provides a general definition of the alcohols, amines or thiols furthermore required as starting materials for carrying out the process (c) according to the invention. In this formula (VI), $R^4$ and X preferably represent those radicals which have already been mentioned as preferred for these substituents in connection with the description of the substances of the formula (I) according to the invention.

The alcohols, amines and thiols of the formula (VI) are generally known compounds of organic chemistry.

Formula (Ie) provides a general definition of the 1-aryl-pyrazoles requires as starting materials for carrying out the process (d) according to the invention. In this formula (Ie), $R^1$, $R^2$, $R^3$, $R^4$, Ar and n preferably represent those radicals which have already been mentioned as preferred for these substituents in connection with the description of the substances of the formula (I) according to the invention.

The 1-aryl-pyrazoles of the formula (Ie) are compounds according to the invention and can be obtained with the aid of the processes (b) or (c) according to the invention.

Formula (VII) provides a general definition of the amines furthermore required as starting materials for carrying out the process (d) according to the invention. In this formula (VII), $R^4$ preferably represents those radicals which have already been mentioned as preferred for this substituent in connection with the description of the substances of the formula (I) according to the invention.

$R^6$ preferably represents straight-chain or branched alkyl having 1 to 6 carbon atoms, particularly preferably straight-chain or branched alkyl having 1 to 4 carbon atoms, in particular methyl or ethyl.

The amines of the formula (VII) are generally known compounds of organic chemistry.

Suitable diluents for carrying out the process (a) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ethers, nitriles, such as acetonitrile or propionitrile, esters, such as ethyl acetate, or sulphoxides, such as dimethyl sulphoxide.

The process (a) according to the invention is preferably carried out in the presence of a suitable reaction auxiliary. Those which are suitable are acids, such as, for example, sulphuric acid or hydrochloric acid, bases, such as, for example, sodium hydroxide, potassium hydroxide or triethylamine, or water-removing agents such as, for example, sodium sulphate or molecular sieve. It is also possible to remove free reaction water from the reaction mixture by azeotropic distillation.

The reaction temperatures can be varied within a relatively wide range in carrying out the process (a) according to the invention. In general, the reaction is carried out at temperatures between $-20°$ C. and $+150°$ C., preferably at temperatures beteen $0°$ C. and $120°$ C.

For carrying out the process (a) according to the invention, 1.0 to 10.0 moles, preferably 1.0 to 5.0 moles of aldehyde or ketone of the formula (III) and if appropriate 0.01 to 5.0 moles, preferably 0.1 to 1.5 moles, of reaction auxiliary are generally employed per mole of 5-amino-1-aryl-pyrazole of the formula (II). The reaction is carried out and the reaction products are worked up and isolated by generally customary methods.

Suitable diluents for carrying out the process (b) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, or alcohols, such as methanol, ethanol or propanol.

However, it is also possible to use a suitable excess of the orthoester or orthoamide of the formula (IV) employed as the reaction partner simultaneously as the diluent.

If necessary, the process (b) according to the invention is carried out in the presence of a suitable reaction auxiliary. Those which are suitable are, in particular, inorganic or organic acids, such as hydrochloric acid, acetic acid or p-toluenesulphonic acid. However, it is also possible to carry out the process (b) according to the invention without the presence of a reaction auxiliary.

The reaction temperatures can be varied within a relatively wide range on carrying out the process (b) according to the invention. In general, the reaction is carried out at temperatures between $-20°$ C. and $+150°$ C., preferably at temperatures between $0°$ C. and $120°$ C.

For carrying out the process (b) according to the invention, 1.0 to 20.0 moles, preferably 1.0 to 10.0 moles of orthoester or orthoamide of the formula (IV) and if appropriate 0.01 to 10.0 moles, preferably 0.1 to 1.5 moles, of reaction auxiliary are generally employed per mole of 5-amino-1-aryl-pyrazole of the formula (II). The reaction is carried out and the reaction products are worked up and isolated by generally customary methods.

Suitable diluents for carrying out the process (c) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, esters, such as ethyl acetate, or sulphoxides, such as dimethyl sulphoxide.

It is also possible to use a suitable excess of the alcohol, amine or thiol of the formula (VI) employed as the reaction partner simultaneously as the diluent.

The process (c) according to the invention is preferably carried out in the presence of a suitable reaction auxiliary. Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a relatively wide range on carrying out the process (c) according to the invention. In general, the reaction is carried out at temperatures between $-20°$ C. and $+150°$ C., preferably at temperatures between $0°$ C. and $120°$ C.

For carrying out the process (c) according to the invention, 1.0 to 20.0 moles, preferably 1.0 to 10.0 moles of alcohol, amine or thiol of the formula (VI) and if appropriate 1.0 to 5.0 moles, preferably 1.0 to 2.0 moles, of reaction auxiliary are generally employed per mole of 5-halogenoalkylideneimino-1-aryl-pyrazole of the formula (V). The reaction is carried out and the reaction products are worked up and isolated by generally customary methods.

Suitable diluents for carrying out the process (d) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, esters, such as ethyl acetate, or sulphoxides, such as dimethyl sulphoxide.

However, it is also possible to use a suitable excess of the amine of the formula (VII) employed as the reaction partner simultaneously as the diluent.

The reaction temperatures can be varied within a relatively wide range in carrying out the process (d) according to the invention. In general, the reaction is carried out at temperatures between $-20°$ C. and $+150°$ C., preferably at temperatures between $0°$ C. and $120°$ C.

For carrying out the process (d) according to the invention, 1.0 to 20.0 moles, preferably 1.0 to 5.0 moles of amine of the formula (VII), are generally employed per mole of 1-arylpyrazole of the formula (Ie). The reaction is carried out and the reaction products are worked up and isolated by generally customary methods.

The active compounds are suitable for combating animal pests, in particular insects, arachnida and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chlorioptes spp., Sarcoptes spp., Tarsonemus spp., *Bryobia praetiosa,* Panonychus spp. and Tetranychus spp.

The active compounds accoring to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas.

They are active against normally sensitive and resistant species and strains, as well as against all parasitic and non-parasitic stages of development of the ectoparasites.

The active compounds according to the invention are distinguished by a strong insecticidal action. They can be employed particularly successfully against insects which are harmful to plants, such as, for example, against the larvae of the mustard beetle (*Phaedon cochleariae*), against the green peach aphid (*Myzus persicae*) or against the black bean aphid (*Aphis fabae*). In this case, the active compounds according to the invention show not only protective but also leaf systemic and root systemic properties.

In addition, the active compounds according to the invention are also suitable for combating soil insects and can be employed, for example, for combating onion fly grubs (*Phorbia antiqua*) in the soil.

In addition, the active compounds according to the invention have a high activity against hygiene pests and stored product pests and can be employed, for example, for combating the German cockroach (*Blattella germanica*). In addition, the active compounds according to the invention can be particularly successfully used for combating pests which live parasitically on warm-blooded animals, such as, for example, against the cattle tick (*Boophilus microplus*).

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and uner normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The administration of the active compounds which can be used according to the invention occurs in this sector in a known fashion, such as by oral administration in the form of, for example, tablets, capsules, potions, granules, by means of dermal or external application in the form of, for example, dipping, spraying, pouring-on, spotting-on and dusting, as well as by means of parenteral administration in the form, for example, of injection, and, furthermore, by means of the feed-through process. In addition, application as moulded articles (collar, ear tag) is also possible.

The biological effectiveness of the compounds according to the invention will be explained with reference to the examples below.

PREPARATION EXAMPLES

Example 1

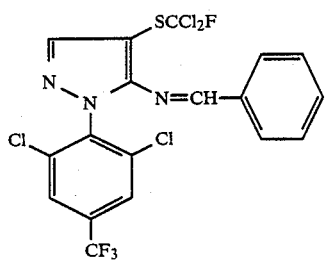

(Process a)

8.6 g (0.02 mol) of 5-amino-1-(2,6-dichloro-4-trifluoromethylphenyl)-4-dichlorofluoromethylthio-pyrazole in 200 ml of anhydrous toluene are heated under reflux for 4 hours in a water separator. 4 drops of concentrated sulphuric acid are then added and 6.4 g (0.06 mol) of freshly distilled benzaldehyde are added over 2 hours. After completion of the addition, the mixture is heated under reflux for a further 16 hours and the liberated reaction water is separated off in a water separator. For working up, the cooled reaction mixture is washed three times using 100 ml of saturated sodium hydrogen carbonate solution in each case, dried over sodium sulphate and concentrated in vacuo. The residue is purified by column chromatography (silica gel; eluent: petroleum ether/ethyl acetate 9:1).

8 g (77% of theory) of 5-benzylideneimino-1-(2,6-dichloro-4-trifluoromethyl-phenyl)-4-dichloro-fluoromethylthio-pyrazole of melting point 75° C. are obtained.

Example 2

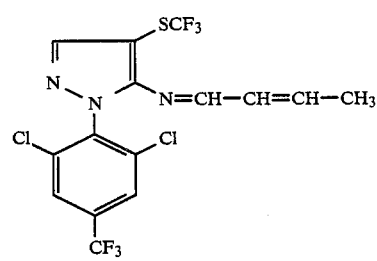

(Process a)

7.9 g (0.02 mol) of 5-amino-1-(2,6-dichloro-4-trifluoromethylphenyl)-4-trifluoromethylthio-pyrazole 2.2 g (0.05 mol) of acetaldehyde, 0.1 g of p-toluenesulphonic acid and 5 g of molecular sieve (BAYLITH TE 144) are stirred at room temperature for 48 hours in 100 ml of toluene, the mixture is then filtered, the filtrate is concentrated in vacuo and the residue is purified by column chromatography (silica gel; eluent: petroleum ether/ethyl acetate).

2.5 g (28% of theory) of 5-but-2-ene-1-ylideneimino-1-(2,6-dichloro-4-trifluoromethyl-phenyl)-4-trifluoromethylthio-pyrazole are obtained as an oil. $^1$H-NMR (CDCl$_3$): $\delta = 1.95$ (d, 3H); 7.9 (s, 1H) ppm. MS: m/e = 447; 449 (M$^+$)

Example 3

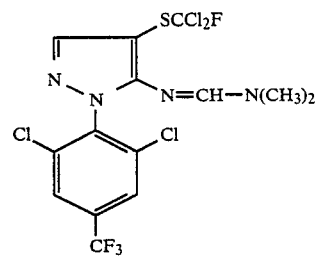

(Process b)

10 g (0.025 mol) of 5-amino-4-dichlorofluoromethylthio-1-(2,6-dichloro-4-trifluoromethyl-phenyl)-pyrazole in 25 ml (0.23 mol) of dimethylformamide dimethyl acetal are heated for 12 hours under reflux, the mixture is then concentrated in vacuo, and the residue is stirred with water, filtered with suction and dried.

11 g (97% of theory) of 5-(N,N-dimethylaminomethylideneimino)-1-(2,6-dichloro-4-trifluoromethyl-phenyl)-4-dichlorofluoromethylthio-pyrazole of melting point 108° C. (decomp.) are obtained.

Example 4

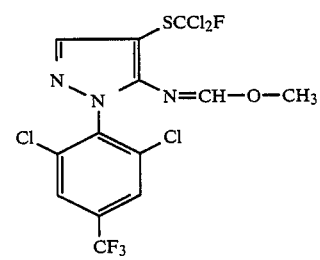

(Process b)

0.5 g of p-toluenesulphonic acid is added to 13.0 g (0.03 mol) of 5-amino-1-(2,6-dichloro-4-trifluoromethyl-phenyl)-4-dichlorofluoromethylthio-pyrazole and 40 ml (0.39 mol) of trimethylorthoformate, and the mixture is heated to reflux for 4 hours. Simultaneously, liberated methanol is removed from the reaction mixture by distillation over a 10 cm long Vigreux column having a descending condenser. For working up, the mixture is concentrated in vacuo, the residue is dissolved in ligroin and filtered through kieselguhr and the solvent is removed in vacuo.

11.5 g (81% of theory) of 5-(methoxymethylideneimino)-1-(2,6-dichloro-4-trifluoromethyl-phenyl)-4-dichlorofluoromethylthio-pyrazole are obtained as an oil. $^1$H-NMR (CDCl$_3$): $\delta = 3.66$ (s, 3H); 7.69 (s, 2H); 7.87 (s, 1H); 8.42 (s, 1H) ppm.

The following 1-aryl-pyrazoles of the general formula (I):

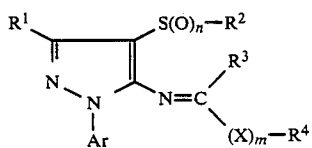

(I)

are obtained in a corresponding manner and according to the general instructions for preparation:

| Ex. No. | $R^1$ | $-S(O)_n-R^2$ | $=C\begin{matrix}R^3\\(X)_m-R^4\end{matrix}$ | Ar | Physical Data |
|---|---|---|---|---|---|
| 5 | H | $-SCCl_2F$ | $=CH-N(CH_3)_2$ | 4-$CF_3$-phenyl | m.p. 77–78° C. |
| 6 | H | $-SCCl_2F$ | $=CH-N(CH_3)_2$ | 2-$OCF_3$-3,5-dibromophenyl | m.p. 92° C. |
| 7 | H | $-SCF_3$ | $=CH-$phenyl | 2,6-dichloro-4-$CF_3$-phenyl | m.p. 85° C. |
| 8 | H | $-SCF_3$ | $=CH-OC_2H_5$ | 2,6-dichloro-4-$CF_3$-phenyl | $^1H$—NMR* 7.9; 8.35 |
| 9 | H | $-SCCl_2F$ | $=CH-$(4-Cl-phenyl) | 2,6-dichloro-4-$CF_3$-phenyl | m.p. 95° C. |
| 10 | H | $-SCCl_2F$ | $=CH-$(3-Cl-phenyl) | 2,6-dichloro-4-$CF_3$-phenyl | m.p. 91° C. |
| 11 | H | $-SCCl_2F$ | $=CH-$(2-Cl-phenyl) | 2,6-dichloro-4-$CF_3$-phenyl | m.p. 105° C. |

-continued

| Ex. No. | R¹ | —S(O)ₙ—R² | =C(R³)(X)ₘ—R⁴ | Ar | Physical Data |
|---|---|---|---|---|---|
| 12 | CH₃ | —SCF₃ | =CH—C₆H₅ | 2,6-Cl₂-4-CF₃-C₆H₂ | ¹H—NMR* 9.05 |
| 13 | H | —S(O)—CCl₂F | =CH—C₆H₅ | 2,6-Cl₂-4-CF₃-C₆H₂ | m.p. 110° C. |
| 14 | H | —SO₂—CCl₂F | =CH—C₆H₅ | 2,6-Cl₂-4-CF₃-C₆H₂ | m.p. 159° C. |
| 15 | H | —SO₂—CF₃ | =CH—C₆H₅ | 2,6-Cl₂-4-CF₃-C₆H₂ | m.p. 132° C. |
| 16 | H | —S(O)—CF₃ | =CH—C₆H₅ | 2,6-Cl₂-4-CF₃-C₆H₂ | m.p. 141° C. |
| 17 | H | —S(O)—CF₃ | =CH—C₆H₄—Cl (4-) | 2,6-Cl₂-4-CF₃-C₆H₂ | m.p. 118° C. |
| 18 | CH₃ | —SCF₃ | =CH—OC₂H₅ | 2,6-Cl₂-4-CF₃-C₆H₂ | m.p. 39–41° C. |
| 19 | CH₃ | —SCCl₂F | =CH—OC₂H₅ | 2,6-Cl₂-4-CF₃-C₆H₂ | m.p. 76–77° C. |

-continued

| Ex. No. | $R^1$ | $-S(O)_n-R^2$ | $=C\begin{matrix}R^3\\(X)_m-R^4\end{matrix}$ | Ar | Physical Data |
|---|---|---|---|---|---|
| 20 | $CH_3$ | $-SO_2-CCl_2F$ | $=CH-OC_2H_5$ | 2,6-Cl$_2$-4-CF$_3$-C$_6$H$_2$ | m.p. 111–112° C. |
| 21 | $CH_3$ | $-\underset{\underset{O}{\parallel}}{S}-CF_3$ | $=CH-OC_2H_5$ | 2,6-Cl$_2$-4-CF$_3$-C$_6$H$_2$ | $n_D^{20}$ 1.5162 |
| 22 | $CH_3$ | $-SO_2-CF_3$ | $=CH-OC_2H_5$ | 2,6-Cl$_2$-4-CF$_3$-C$_6$H$_2$ | m.p. 67–68° C. |
| 23 | $CH_3$ | $-SCF_3$ | $=C\begin{matrix}CH_3\\OCH_3\end{matrix}$ | 2,6-Cl$_2$-4-CF$_3$-C$_6$H$_2$ | $n_D^{20}$ 1.5069 |
| 24 | $CH_3$ | $-SCF_3$ | $=C\begin{matrix}C_2H_5\\OC_2H_5\end{matrix}$ | 2,6-Cl$_2$-4-CF$_3$-C$_6$H$_2$ | $n_D^{20}$ 1.5064 |
| 25 | $CH_3$ | $-SCF_3$ | $=CH-OCH_3$ | 2,6-Cl$_2$-4-CF$_3$-C$_6$H$_2$ | m.p. 80–81° C. |
| 26 | $CH_3$ | $-SCF_3$ | $=C\begin{matrix}CH_3\\OC_2H_5\end{matrix}$ | 2,6-Cl$_2$-4-CF$_3$-C$_6$H$_2$ | $n_D^{20}$ 1.520 |
| 27 | H | $-\underset{\underset{O}{\parallel}}{S}-CF_3$ | $=CH-$(3-Cl-C$_6$H$_4$) | 2,6-Cl$_2$-4-CF$_3$-C$_6$H$_2$ | m.p. 108° C. |

-continued

| Ex. No. | R¹ | —S(O)$_n$—R² | =C(R³)(X)$_m$—R⁴ | Ar | Physical Data |
|---|---|---|---|---|---|
| 28 | H | —S(=O)—CCl₂F | =CH—(3-Cl-C₆H₄) | 2,6-Cl₂-4-CF₃-C₆H₂ | m.p. 110° C. |
| 29 | CH₃ | —SCCl₂F | =CH—C₆H₅ | 2,6-Cl₂-4-CF₃-C₆H₂ | m.p. 127° C. |
| 30 | CH₃ | —SCF₃ | =CH—(4-Cl-C₆H₄) | 2,6-Cl₂-4-CF₃-C₆H₂ | m.p. 104° C. |
| 31 | CH₃ | —SCCl₂F | =CH—(4-Cl-C₆H₄) | 2,6-Cl₂-4-CF₃-C₆H₂ | m.p. 125° C. |
| 32 | CH₃ | —SCF₃ | =CH—(4-OCH₃-C₆H₄) | 2,6-Cl₂-4-CF₃-C₆H₂ | m.p. 130–135° C. |
| 33 | CH₃ | —SCCl₂F | =CH—(4-OCH₃-C₆H₄) | 2,6-Cl₂-4-CF₃-C₆H₂ | m.p. 97–99° C. |
| 34 | CH₃ | —SCF₃ | =CH—(4-CH₃-C₆H₄) | 2,6-Cl₂-4-CF₃-C₆H₂ | m.p. 120–123° C. |
| 35 | CH₃ | —SCCl₂F | =CH—(4-CH₃-C₆H₄) | 2,6-Cl₂-4-CF₃-C₆H₂ | m.p. 122–125° C. |

-continued

| Ex. No. | R¹ | —S(O)ₙ—R² | =C(R³)(X)ₘ—R⁴ | Ar | Physical Data |
|---|---|---|---|---|---|
| 36 | CH₃ | —SCF₃ | =CH—(3,4-dichlorophenyl) | 2,6-dichloro-4-(CF₃)phenyl | m.p. 94° C. |
| 37 | CH₃ | —SCCl₂F | =CH—(3,4-dichlorophenyl) | 2,6-dichloro-4-(CF₃)phenyl | m.p. 91° C. |
| 38 | CH₃ | —SCF₃ | =CH—(3-chlorophenyl) | 2,6-dichloro-4-(CF₃)phenyl | m.p. 110–112° C. |
| 39 | CH₃ | —SCCl₂F | =CH—(3-chlorophenyl) | 2,6-dichloro-4-(CF₃)phenyl | m.p. 59–62° C. |
| 40 | CH₃ | —SCF₃ | =CH—phenyl | 2-F-6-Cl-4-(CF₃)phenyl | m.p. 83–84° C. |
| 41 | CH₃ | —S(O)—CF₃ | =CH—phenyl | 2-F-6-Cl-4-(CF₃)phenyl | m.p. 89–90° C. |
| 42 | H | —SCCl₂F | =CH—phenyl | 2-F-6-Cl-4-(CF₃)phenyl | m.p. 103–109° C. |
| 43 | H | —S(O)—CCl₂F | =CH—phenyl | 2-F-6-Cl-4-(CF₃)phenyl | m.p. 88–94° C. |

-continued

| Ex. No. | R¹ | —S(O)ₙ—R² | =C< R³ / (X)ₘ—R⁴ | Ar | Physical Data |
|---|---|---|---|---|---|
| 44 | H | —SO₂—CCl₂F | =CH—(phenyl) | 3-Cl, 2-F, 4-CF₃ phenyl | m.p. 116–122° C. |

USE EXAMPLES

The compounds shown below were employed as comparison substances in the following use examples:

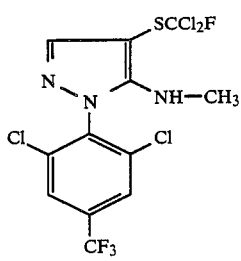

(A)

5-(N-Methylamino)-1-(2,6-dichloro-4-trifluoromethyl-phenyl)-4-dichlorofluoromethylthio-pyrazole

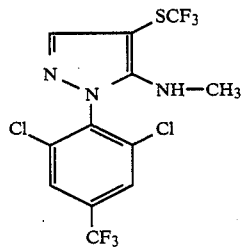

(B)

5-(N-Methylamino)-1-(2,6-dichloro-4-trifluoromethyl-phenyl)-4-trifluoromethylthio-pyrazole (both known from EP 201,852)

EXAMPLE A

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the following compounds of the preparation examples show a superior activity compared to the prior art: 10, 17, 28, 41, 43, 44.

EXAMPLE B

Aphis Test (Systemic Action)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the black bean aphid (*Aphis fabae*) are each watered with 20 ml of the preparation of the active compound of the desired concentration in such a way that the preparation of the active compound penetrates into the soil without wetting the shoot. The active compound is taken up by the roots and passes to the shoot.

After the specified periods of time, the destruction in % is determined. 100% means that all the aphids have been killed; 0% means that none of the aphids have been killed.

In this test, for example, the following compounds of the preparation examples show a superior activity compared to the prior art: 2 and 8.

EXAMPLE C

Critical Concentration Test/Soil Insects

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compound of the preparation examples shows a superior activity compared to the prior art: 1.

EXAMPLE D

Crictical Concentration Test/Root-Systemic Action

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, for example, the following compounds of the preparation examples show a superior action compared to the prior art: 2, 7 and 8.

EXAMPLE E

Critical Concentration Test/Root-Systemic Action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, for example, the following compound of the preparation examples shows a superior action compared to the prior art: 8.

EXAMPLE F

LT$_{100}$ Test D

Test animals: *Blattella germanica*
Number of test animals: 10
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filterpaper of about 9.5 cm diameter is located on the bottom of the Petri dish. The Petri dish is left standing open until the solvent has completely evaporated. The amount of active compound per m$^2$ of filterpaper varies, depending on the concentration of the active compound solution. The stated number of test animals is then introduced into the Petri dish, and the dish is covered with a glass lid.

The condition of the test animals is checked 3 days after commencement of the test. The destruction in % is determined. 100% means that all the test animals have been killed; 0% means that none of the test animals have been killed.

In this test, for example, the following compound of the preparation examples shows a superior action compared to the prior art: 2.

EXAMPLE G

Test With *Boophilus microplus* resistant/OP-resistant Biarra strain

Solvent:
 35 parts by weight of ethylene glycol monomethyl ether
 35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compound of the preparation examples shows a superior action compared to the prior art: 4.

What is claimed is:
1. A 1-arylpyrazole of the formula

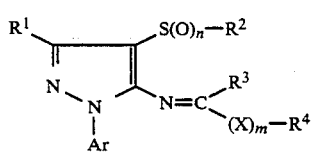

in which
 R$^1$ represents hydrogen, alkyl or halogenoalkyl,

R² represents alkyl, halogenoalkyl, unsubstituted or substituted aralkyl or unsubstituted or substituted aryl, R³ represents hydrogen, alkyl or halogenoalkyl, R⁴ represents alkyl, alkenyl, alkinyl, halogenoalkyl, halogenoalkenyl, halogenoalkinyl or in each case unsubstituted or substituted aryl or heteroaryl, X represents oxygen, sulphur or an N-alkyl radical, Ar represents in each case an unsubstituted or substituted phenyl or pyridyl, m represents a number 0 or 1 and n represents a number 0, 1 or 2.

2. A 1-arylpyrazole according to claim 1, in which

R¹ represents hydrogen, alkyl having 1 to 4 carbon atoms or halogenoalkyl having in each case 1 to 4 carbon atoms and 1 to 9 identical or different halogen atoms, R² represents alkyl having 1 to 8 carbon atoms, halogenoalkyl having 1 to 8 carbon atoms and 1 to 17 identical or different halogen atoms, phenyl or phenylalkyl, the phenylalkyl having 1 to 4 carbon atoms in the alkyl part and said phenyl and phenylalkyl being unsubstituted or substituted in the phenyl part by halogen, cyano, nitro, alkyl, alkoxy, alkylthio, alkylsulphinyl or alkylsulphonyl having in each case 1 to 4 carbon atoms in the individual alkyl part, halogenoalkyl, halogenoalkoxy, halogenoalkylthio, halogenoalkylsulphinyl or halogenoalkylsulphonyl having in each case 1 to 4 carbon atoms in the individual alkyl parts and 1 to 9 identical or different halogen atoms, R³ represents hydrogen, alkyl having 1 to 8 carbon atoms or halogenoalkyl having 1 to 8 carbon atoms and 1 to 17 identical or different halogen atoms, R⁴ represents alkyl, alkenyl or alkinyl having in each case up to 8 carbon atoms, halogenoalkyl, halogenoalkenyl or halogenoalkinyl having in each case up to 8 carbon atoms, and 1 to 17 identical or different halogen atoms, or phenyl or heteroaryl having 1 to 9 carbon atoms and 1 to 3 hetero atoms selected from nitrogen, oxygen and/or sulphur and in each case being unsubstituted or substituted by halogen, cyano, nitro, alkyl, alkoxy, alkylthio, alkylsulphinyl or by alkylsulphonyl having in each case 1 to 4 carbon atoms in the individual alkyl part, X represents oxygen, sulphur or an N-alkyl having 1 to 6 carbon atoms in the alkyl part, Ar represents phenyl, 2-pyridyl, 3-pyridyl or 4-pyridyl which in each case being unsubstituted or substituted by cyano, nitro, halogen, alkyl, alkoxy or alkoxycarbonyl having in each case 1 to 4 carbon atoms, halogenoalkyl or halogenoalkoxy having in each case 1 to 4 carbon atoms and 1 to 9 identical or different halogen atoms or a radical —S(O)Hd p—R⁷, in which R⁷ represents amino, alkyl, alkylamino, dialkylamino having in each case 1 to 4 carbon atoms in the individual alkyl parts or halogenoalkyl having 1 to 4 carbon atoms and 1 to 9 identical or different halogen atoms, m represents a number 0 or 1, n represents a number 0, 1 or 2 and p represents a number 0, 1 or 2.

3. A 1-arylpyrazole according to claim 1, in which

R¹ represents hydrogen, methyl, ethyl, n- or i-propyl and trifluoromethyl,

R² represents methyl, ethyl, n- or i-propyl, n-, i-, s- or t-butyl, n- or i-pentyl, n- or i-hexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, or phenyl, benzyl or phenylethyl which is in each case unsubstituted, or substituted by fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, R³ represents hydrogen, methyl, ethyl, n- or i-propyl, n-, i-, s- or t-butyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, dichloromethyl, chloropropyl, bromopropyl, chlorofluoromethyl, trichloromethyl, trifluoroethyl, trifluorochloroethyl, tetrafluoroethyl, difluorochloroethyl, fluorodibromomethyl, difluorobromomethyl or fluorochlorobromomethyl, R⁴ represents methyl, ethyl, n- or i-propyl, n-, i, s- or t-butyl, n- or i-pentyl, n- or i-hexyl, vinyl, propenyl, allyl, n- or i-butenyl, n- or i-pentenyl, propargyl, n- or i-butinyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorochlorobromomethyl, difluorobromomethyl fluorochlorobromomethyl, chloroallyl, fluoroallyl, chlorobutenyl, fluorobutenyl, dichloroallyl, fluorochlorallyl, dichlorobutenyl, difluoroallyl, bromoallyl, or phenyl, pyridyl, furyl or thienyl which is in each case unsubstituted or substituted by fluorine, chlorine, bromine, iodine, cyano, nitro, methyl, ethyl, methoxy, methylthio, trifluoromethyl, methylsulphinyl, methylsulphonyl, trifluromethoxy, trifluoromethylthio, trifluoromethylsulphinyl or trifluoromethylsulphonyl, X represents oxygen, sulphur or an N-alkyl radical having 1 to 4 carbon atoms in the alkyl part, Ar represents phenyl or 2-pyridyl which is in each case unsubstituted or substituted by cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $-S(O)_p-R^7$ in which $R^7$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, m represents a number 0 or 1, n represents a number 0, 1 or 2 and p represents a number 0, 1 or 2.

4. A 1-arylpyrazole according to claim 1, in which $R^1$ represents hydrogen or methyl, $R^2$ represents methyl, ethyl, trifluoromethyl, dichlorofluoromethyl or chlorodifluoromethyl, $R^3$ represents hydrogen, methyl, ethyl, n- or i-propyl or trifluoromethyl, $R^4$ represents methyl, ethyl, n- or i-propyl, n-, i-, s- or t-butyl, vinyl, propenyl, allyl, n- or i-butenyl, or phenyl which is unsubstituted or substituted by fluorine, chlorine, bromine, methyl or trifluoromethyl, X represents oxygen, sulphur, an N-methyl radical or an N-ethyl radical, Ar represents phenyl which is unsubstituted or substituted by fluorine, chlorine, bromine, methyl, ethyl, methoxy, ethoxy, trifluoromethyl, trifuloromethoxy, trifluoromethylthio, trifluoromethylsulphinyl or trifluoromethylsulphonyl, m represents a number 0 or 1 and n represents a number 0, 1 or 2.

5. A pesticidal composition comprising a pesticidally effective amount of at least one 1-arylpyrazole according to claim 1 and a suitable extender or carrier.

6. A method of combating pests comprising applying to said pests or to a habitat thereof a pesticidally effective amount of a 1-arylpyrazole according to claim 1.

7. A method of combating insects comprising applying to said insects or a habitat thereof an insecticidally effective amount of a 1-arylpyrazole according to claim 1.

* * * * *

UNITED STATES PATENT AND TRADEMARK OFFICE
CERTIFICATE OF CORRECTION

PATENT NO. : 4,863,937

DATED : September 5, 1989

INVENTOR(S) : Reinhold Gehring, et al.

It is certified that error appears in the above-identified patent and that said Letters Patent is hereby corrected as shown below:

| | |
|---|---|
| Title Page, "Inventors", line 2 | Delete "Korte-Jensen" and substitute --Jensen-Korte-- |
| Col. 8, line 5 | Delete heading |
| Col. 9, line 59 and Col. 11, line 2 | Delete "requires" and substitute --required-- |
| Col. 10, line 52 | After "as" insert --,-- |
| Col. 11, line 36 | Delete "ethers" and substitute --ether-- |
| Col. 14, line 57 | Correct --Chorioptes-- |
| Col. 15, line 56 | Delete "uner" and substitute --under-- |

UNITED STATES PATENT AND TRADEMARK OFFICE
CERTIFICATE OF CORRECTION

PATENT NO. : 4,863,937      Page 2 of 4
DATED : September 5, 1989
INVENTOR(S) : Reinhold Gehring, et al.

It is certified that error appears in the above-identified patent and that said Letters Patent is hereby corrected as shown below:

| Active Compounds | Concentration or active compound in % | Degree of Destruction in % after 3d |
|---|---|---|
| (known) pyrazole with SCF$_3$, NH-CH$_3$, N-(2,6-dichloro-4-trifluoromethylphenyl) | 0.0001<br>0.00001 | 100<br>0 |
| (17) pyrazole with SOCF$_3$, N=CH-(4-Cl-C$_6$H$_4$), N-(2,6-dichloro-4-trifluoromethylphenyl) | 0.0001<br>0.00001 | 100<br>80 |
| (28) pyrazole with SOCCl$_2$F, N=CH-(3-Cl-C$_6$H$_4$), N-(2,6-dichloro-4-trifluoromethylphenyl) | 0.0001<br>0.00001 | 100<br>80 |

UNITED STATES PATENT AND TRADEMARK OFFICE
CERTIFICATE OF CORRECTION

PATENT NO. : 4,863,937                              Page 3 of 4
DATED      : September 5, 1989
INVENTOR(S): Reinhold Gehring, et al.

It is certified that error appears in the above-identified patent and that said Letters Patent is hereby corrected as shown below:

| Active Compounds | Concentration or active compound in % | Degree of Destruction in % after 3d |
|---|---|---|
| (41) | 0.0001 | 100 |
|      | 0.00001 | 100 |
| (43) | 0.0001 | 100 |
|      | 0.00001 | 100 |
| (44) | 0.0001 | 100 |
|      | 0.00001 | 100 |

UNITED STATES PATENT AND TRADEMARK OFFICE
CERTIFICATE OF CORRECTION

PATENT NO. : 4,863,937

DATED : September 5, 1989

INVENTOR(S) : Reinhold Gehring, et al.

It is certified that error appears in the above-identified patent and that said Letters Patent is hereby corrected as shown below:

Col. 33, line 55    Delete "$-S(O)Hd_p-R^7$" and substitute $--S(O)_p-R^7--$

Col. 34, line 44    Correct spelling of --fluorodibromomethyl--

Signed and Sealed this

Eleventh Day of May, 1993

Attest:

MICHAEL K. KIRK

*Attesting Officer*    Acting Commissioner of Patents and Trademarks